United States Patent
Pearce et al.

(10) Patent No.: US 10,358,430 B2
(45) Date of Patent: Jul. 23, 2019

(54) OLIGOMERIC (TH)FP, PRODUCTION AND USES THEREFOR

(71) Applicant: Thomas Swan & Co. Ltd, Durham (GB)

(72) Inventors: Ian Stuart Pearce, Hexham (GB); David Dunn, Jarrow (GB); Howard Winston Tyrrell Sutton, Washington (GB); John Ing Chuan Daly, Hexham (GB); Simon Jonathon Grant, Newcastle (GB)

(*) Notice: Subject to any disclaimer, the term of this patent is extended or adjusted under 35 U.S.C. 154(b) by 29 days.

(21) Appl. No.: 15/686,949

(22) Filed: Aug. 25, 2017

(65) Prior Publication Data

US 2019/0062291 A1 Feb. 28, 2019

(51) Int. Cl.
*C07D 307/36* (2006.01)
*C07D 307/06* (2006.01)
*C08F 36/06* (2006.01)

(52) U.S. Cl.
CPC ......... *C07D 307/36* (2013.01); *C07D 307/06* (2013.01); *C08F 36/06* (2013.01)

(58) Field of Classification Search
CPC ................. C08F 236/10; C08L 47/00
USPC ............ 428/36.9; 525/332.9, 332.5; 524/572
See application file for complete search history.

(56) References Cited

U.S. PATENT DOCUMENTS

| | | | |
|---|---|---|---|
| 2012/0259082 A1 | 10/2012 | Hogan et al. | |
| 2015/0086735 A1* | 3/2015 | Valenti | C08F 36/06 428/36.9 |
| 2017/0029394 A1 | 2/2017 | Dunn et al. | |

FOREIGN PATENT DOCUMENTS

| CN | 103374101 A | 10/2013 |
|---|---|---|
| EP | 1 462 459 A1 | 11/2002 |
| EP | 2 495 267 A1 | 3/2011 |
| WO | 2011/087841 A1 | 7/2011 |
| WO | 2016/046575 A1 | 3/2016 |

* cited by examiner

*Primary Examiner* — William K Cheung
(74) *Attorney, Agent, or Firm* — Brian J. Pangrle

(57) ABSTRACT

A method for the isolation of oligomeric 2, 2-difurylpropane (DTHFP) suitable for use on an industrial scale. A method can include using oligomeric 2, 2-difurylpropane, in particular, its use can be as a polar modifier for butadiene and styrene butadiene polymerization so is to produce rubber. Utilizing the material as an alternative to DTHFP in rubber production avoids subsequent leaching of the DTHFP into the environment as the oligomeric 2, 2-difurylpropane (DTHFP) gives rise to much lower levels of leaching.

20 Claims, No Drawings

OLIGOMERIC (TH)FP, PRODUCTION AND USES THEREFOR

BACKGROUND

Various embodiments relate to a process for the preparation of a composition suitable for isolation of oligomeric poly (2, 5-furylpropane), termed pFP, and oligomeric 2, 5-poly(terahydrofurylpropane), termed pTHFP, using a simple and energy efficient isolation process with limited decomposition.

A related material, DTHFP (2, 2-difurylpropane), is an established speciality chemical used in the preparation of butadiene rubber (BR or polybutadiene) is in conjunction with a lithium catalyst. Its use is exemplified in, for example, U.S. 2012/0259082 where a high level of the meso-isomer has been shown to increase the vinyl content of polymerised 1,3-butadiene.

In developing synthetic routes to high level meso-isomer DTHFP, by-product pFP and pTHFP have been identified from some routes. This is currently treated as waste, with associated costs (e.g., disposal costs).

Uses for pFP and pTHFP would make some routes to high yield meso-DTHFP more commercially attractive, particularly from some routes to high meso DTHFP production. The provision of a method to isolate and use oligomeric DTHFP is of interest as it would convert an otherwise undesirable by-product of a process into an available chemical with potential commercial uses.

SUMMARY

Various embodiments pertain to methods for the synthesis, isolation and use of oligomeric pFP and pTHFP. Further, pFP and particularly pTHFP have been found to be useful in butadiene rubber synthesis and subsequent processing when left in combination with DTHFP (2, 2-difurylpropane). Various embodiments pertain to a method of production of oligomeric pFP and pTHFP in compositions from which isolation may be readily facilitated. Various embodiments provide examples of uses for oligomeric pFP and pTHFP.

DETAILED DESCRIPTION

The following description includes the best mode presently contemplated for practicing the described implementations. This description is not to be taken in a limiting sense, but rather is made merely for the purpose of describing general principles of various implementations. The scope of invention should be ascertained with reference to issued claims.

Various embodiments pertain to methods for the synthesis, isolation and use of oligomeric pFP and pTHFP. Further, pFP and particularly pTHFP have been found to be useful in butadiene rubber synthesis and subsequent processing when left in combination with DTHFP (2, 2-difurylpropane). Various embodiments pertain to a method of production of oligomeric pFP and pTHFP in compositions from which isolation may be readily facilitated. Various embodiments provide examples of uses for oligomeric pFP and pTHFP.

DTHFP 2,2-di(tetrahydrofuryl)propane has the formula:

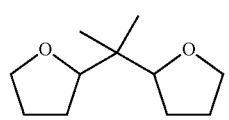

(i)

2,2-di(2-furyl) propane has the formula:

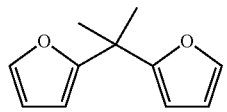

(ii)

Trimeric FP has the formula:

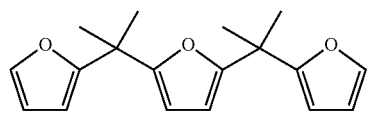

(iii)

Tetrameric FP has the formula:

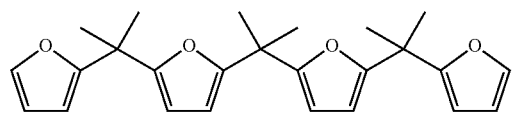

(iv)

Pentameric FP has the formula:

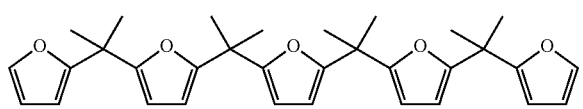

(v)

Oligomeric pFP has the formula:

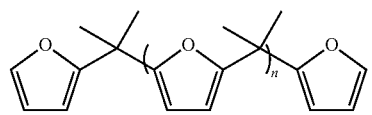

(vi)

n=1 to x and x is greater than 2, x is preferably less than 20.

Oligomeric pTHFP has the formula

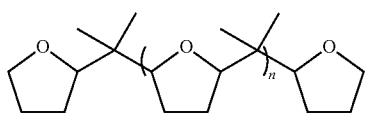

(vii)

n=1 to x and x is greater than 2, x is preferably less than 20.

The hydrogen atoms present in the above structures may be replaced by methyl, ethyl or propyl moieties. Specifically, the methyl moieties in (vi) and vii) may be replaced by ethyl moieties.

Thus, a method can include synthesising oligomeric pFP, the method including the reaction scheme:

Scheme (i)

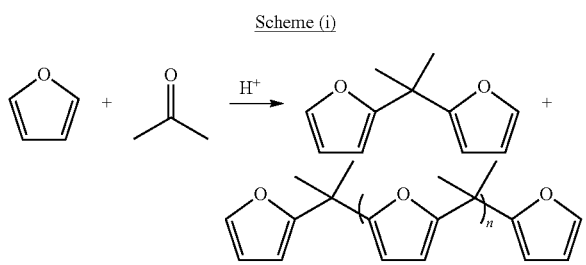

Wherein, as in other pFP structures disclosed herein the hydrogen atoms inherent in the above structures may be individually and separately replaced by methyl, ethyl or propyl moieties. The oligomeric FP may be isolated from the FP by distillation of the DFP from the mixture and isolation of the oligomeric pFP by precipitation on cooling or by chromatography.

Is has been found that oligomeric pFP has a low solubility in FP from which it may be readily separated. In particular, the material may be separated by providing a negative temperature gradient such that the solution is called in which case oligomeric pFP preferentially arises as a suspension. Alternatively, placing a hot surface in the solution can give rise to the position of oligomeric FP onto said surface, such as a glass or steel surface.

In various embodiments, a method provides for the isolation of oligomeric pFP, the method including:
  providing a composition including FP in which oligomeric pFP is dissolved;
  selectively removing DTHFP to provide said solution wherein the FP content is less than 20% by weight; and
  separating said oligomeric DTHFP by providing a temperature gradient in the solution, the temperature gradient being in excess of 50° C. between bulk composition and a solid surface, the solid surface being the cooler and the bulk composition being at a temperature of between 50° C. and 100° C.

As mentioned previously some, i.e. not all synthetic routes to DTHFP give rise to oligomeric pTHFP. For example, further polymerisation can destroy oligomer. A method to produce DTHFP is disclosed in U.S. Ser. No. 15/302,936, filed Jul. 10, 2016 which is incorporated herein by reference. pTHFP cannot be produced by all methods, but can be produced by, the method of Table 4 using $Li_2B_4O_7$ based catalyst with THF to produce pTHFP from pFP in FP. The FP, pFP composition being obtainable as above.

Is has been found that oligomeric pTHFP has a low solubility in a D, L, racemic mixture of DTHFP from which it may be readily separated. In particular, the material may be separated by providing a negative temperature gradient such that the solution is called in which case oligomeric pTHFP preferentially arises as a suspension. Alternatively, placing a hot surface in the solution can give rise to the position of oligomeric pTHFP onto said surface, such as a glass or steel surface.

In various embodiments, a method provides for the isolation of oligomeric pTHFP, where the method can include:
  providing a composition including DTHFP in D, L and meso isomeric forms in which oligomeric pTHFP is dissolved;
  selectively removing DTHFP to provide said solution wherein the DTHFP content is less than 20% preferably less than 5% by weight; and
  separating said oligomeric DTHFP by providing a temperature gradient in the solution, the temperature gradient being in excess of 50° C. between bulk composition and a solid surface, the solid surface being the cooler and the bulk composition being at a temperature of between 50° C. and 100° C. Further isolation may be carried out by filtration or centrifugation.

In various embodiments, a further aspect provides a glass or steel surface coated with oligomeric DTHFP. Such a surface may be arrived at as mentioned above by placing a heated surface to be coated in contact with said solution or the oligomeric DTHFP obtained from suspension, separated by conventional means, may be taken up in a solvent, such as tetrahydrofuran, and painted onto a suitable glass or steel surface and the solvent evaporated to provide a coating. Such coatings have been found to give oxidation resistance to mild steel and a degree of etch resistance to the glass. In addition, the presence of oligomeric pFP and oligomeric THFP in butadiene rubber and butadiene rubber copolymers may reduce wear, such as corrosion induced wear in steel moulds used for making tyres and associated conveying equipment for transferring the rubber to the moulds. This appears to be due to oligomeric pFP and oligomeric THFP lubricating/protecting steel into which it comes into contact. These effects are relevant to automobile tyre manufacture. Addition of oligomeric DTHFP to butadiene rubber may provide a lubricating effect on metal surfaces and so reduce equipment wear in rubber production and subsequent use of rubbers containing oligomeric DTHFP, such as abrasion induced wear in steel moulds used for making tyres and associated conveying equipment for transferring the rubber to the moulds.

Whilst not wishing to be bound by theory it is thought that oligomeric pTHFP interacts less with the polymerisation reaction of butadiene and remains as a relatively mobile species in the finished rubber where it can migrate to the surface of the rubber and produce the above effects. For this effect n in formula vii is preferably 2, 3 or 4, preferably 3 or 4.

As such, various embodiments relate to a composition for coating glass and steel articles, the composition including oligomeric pTHFP dissolved a solid solution of a butadiene or butadiene based rubber.

In a further aspect, it is been found that the known use of DTHFP as a polymerisation regulator for the lithium initiated polarisation of butadiene, such as for example, to produce a styrene butadiene polymer can be improved by providing the DTHFP in a composition including oligomeric pTHFP. It is known, for example from EP 2495267 A1, that DTHFP provides accelerated polymerisation for the production of styrene butadiene rubber. Such known uses relate to the statistical composition including 1:1:2 D:L:Meso DTHFP. More recently it has been found as disclosed in WO 2011087841 that meso DTHFP provides improved vinyl content of styrene butadiene rubber. The disclosure also provides that a racemic D, L mixture of DTHFP provides low vinyl content polymer. Low vinyl content polymers have specific end uses. However, it is advantageous if low vinyl content is accompanied by a block polymeric structure in which multiple repeat units of styrene and butadiene are present to provide a block copolymer.

Being aware of the above affects the sister compounds including oligomeric pTHFP were speculated as being capable of affecting polymerisation kinetics. However, no basis for predicting effects was available and the available information gives every reason to believe that oligomeric pTHFP should either not be used or should be avoided.

It has been found that the use of oligomeric THFP has been of limited effectiveness as a polarisation randomiser for use in conjunction with or as a replacement for THFP. However, it was surprisingly found that an issue of DTHFP leaching from polymerised rubber, was substantially reduced. In particular, oligomeric DTHFP and more specifically were n=1 to 10, or preferably were n=5 to 10 is substantially bound in poly butadiene and copolymers and its loss by leaching as an environmental contaminant is reduced.

Further it has been found that the inclusion of pTHFP with DTHFP in the lithium initiated polarisation of butadiene such as described in EP 2495267 A1, which is incorporated by reference can improve one or more of vinyl content of the polymer (higher), hysteresis of the polymer (lower), wear resistance (lower) and friction losses (lower) in contact with surfaces, such as of an automobile tyre on a roadway.

In the event that chemical names contradict the structures provided the structures prevail.

Although examples of methods, devices, systems, etc., have been described in language specific to structural features and/or methodological acts, it is to be understood that the subject matter defined in the appended claims is not necessarily limited to the specific features or acts described. Rather, the specific features and acts are disclosed as examples of forms of implementing the claimed methods, devices, systems, etc.

The invention claimed is:

1. A steel surface coated at least in part with an oligomer, the oligomer having the structure:

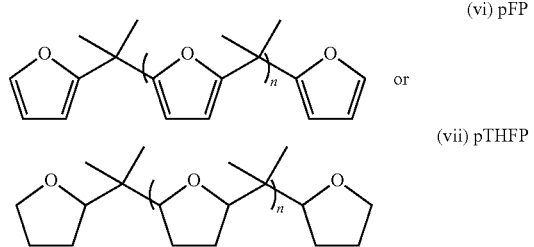

wherein n=1 to x and x is greater than 2.

2. The steel surface of claim 1, the oligomer being in admixture with a butadiene and butadiene copolymers rubber.

3. The steel surface of claim 1, the oligomer being in admixture with DTHFP.

4. The steel surface of claim 3, wherein the weight ratio of oligomer to DTHFP is from 1:40 to 1:1.

5. The steel surface of claim 1 comprising the oligomer in a composition that comprises a butadiene polymer or a butadiene co polymer.

6. The steel surface of claim 5, wherein the composition comprises lithium by being produced by lithium initiated polymerisation of butadiene in the presence of the oligomer.

7. The steel surface of claim 5, wherein the composition comprises a form of an automotive tyre.

8. The steel surface of claim 7, wherein the composition comprises DTHFP at least in part bound by the butadiene polymer or the butadiene co polymer, wherein the butadiene polymer or the butadiene co polymer reduces leaching of the oligomeric DTHFP to the environment.

9. The steel surface of claim 1, wherein x is less than 20.

10. An oligomer for use in the polymerisation of butadiene and butadiene copolymers, the oligomer having the structure:

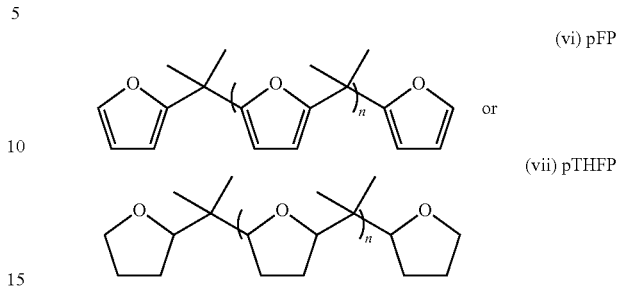

wherein n=1 to x and x is greater than 2, wherein the oligomer is in admixture with DTHFP, and wherein the weight ratio of oligomer to DTHFP is from 1:40 to 1:1.

11. The oligomer of claim 10 in admixture with a butadiene and butadiene copolymers rubber.

12. The oligomer of claim 10 being in a composition that comprises a butadiene polymer or a butadiene co polymer.

13. The oligomer of claim 12, wherein the composition comprises lithium by being produced by lithium initiated polymerisation of butadiene in the presence of the oligomer.

14. The oligomer of claim 12, wherein the composition reduces wear in a steel surface which the composition abrades.

15. The oligomer of claim 12, wherein the composition comprises a form of an automotive tyre.

16. The oligomer of claim 12, wherein the composition comprises at least a portion of the DTHFP bound by the butadiene polymer or the butadiene co polymer, wherein the butadiene polymer or the butadiene co polymer reduces leaching of the oligomeric DTHFP to the environment.

17. The oligomer of claim 10, wherein x is less than 20.

18. A metal surface coated at least in part with an oligomer, the oligomer having the structure:

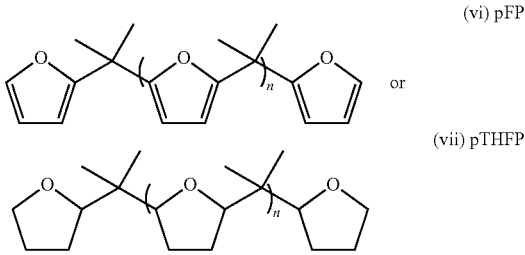

wherein n=1 to x and x is greater than 2, wherein the oligomer is in admixture with DTHFP, and wherein the weight ratio of oligomer to DTHFP is from 1:40 to 1:1.

19. The metal surface of claim 18, wherein the admixture is in the form of an automotive tyre.

20. The metal surface of claim 18, wherein x is less than 20.

* * * * *